(12) United States Patent
Kim et al.

(10) Patent No.: US 11,590,150 B2
(45) Date of Patent: Feb. 28, 2023

(54) PHARMACEUTICAL COMPOSITION FOR PREVENTING OR TREATING ADVERSE DRUG REACTIONS BY STATIN

(71) Applicant: INDUSTRY-ACADEMIC COOPERATION FOUNDATION, YONSEI UNIVERSITY, Seoul (KR)

(72) Inventors: Beom Seok Kim, Seoul (KR); Chui Hoon Kim, Gyeonggi-do (KR); Jong Jin Yoon, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 16/761,764

(22) PCT Filed: Nov. 5, 2018

(86) PCT No.: PCT/KR2018/013307
§ 371 (c)(1),
(2) Date: May 5, 2020

(87) PCT Pub. No.: WO2019/088781
PCT Pub. Date: May 9, 2019

(65) Prior Publication Data
US 2020/0261480 A1    Aug. 20, 2020

(30) Foreign Application Priority Data
Nov. 6, 2017  (KR) .......................... 10-2017-0146515

(51) Int. Cl.
| | | |
|---|---|---|
| *A61K 31/683* | (2006.01) | |
| *A61K 31/137* | (2006.01) | |
| *A61K 31/191* | (2006.01) | |
| *A61K 31/357* | (2006.01) | |
| *A61K 31/496* | (2006.01) | |
| *A61K 31/397* | (2006.01) | |
| *A61K 31/4418* | (2006.01) | |
| *A61K 31/445* | (2006.01) | |

(52) U.S. Cl.
CPC .......... *A61K 31/683* (2013.01); *A61K 31/137* (2013.01); *A61K 31/191* (2013.01); *A61K 31/357* (2013.01); *A61K 31/496* (2013.01); *A61K 31/397* (2013.01); *A61K 31/445* (2013.01); *A61K 31/4418* (2013.01)

(58) Field of Classification Search
None
See application file for complete search history.

(56) References Cited

U.S. PATENT DOCUMENTS

| | | |
|---|---|---|
| 6,083,979 A | 7/2000 | Sebti |
| 2008/0031985 A1 | 2/2008 | Tan |
| 2009/0233843 A1 | 9/2009 | Marin |
| 2017/0281713 A1 | 10/2017 | Crum |

FOREIGN PATENT DOCUMENTS

| | | |
|---|---|---|
| KR | 10-2007-0100781 A | 10/2007 |
| KR | 10-2009-0028983 A | 3/2009 |
| KR | 10-2011-0074833 A | 7/2011 |
| KR | 10-2013-0074808 A | 7/2013 |
| WO | 2010126579 A1 | 11/2010 |

OTHER PUBLICATIONS

Wills et al., , Am. Fam. Physician. Jul. 15, 2005, 72(2), pp. 1-3. (https://www.aafp.org/afp/2005/0715/ol2.html) (Year: 2005).*
S Krishnan-Natesan, "Terbinafine: a pharmacological and clinical review", 2009, Expert Opinion on Pharmacotherapy, 10(16), pp. 2723-2733. (DOI: 10.1517/14656560903307462) (Year: 2009).*
Eljaaly et al., "An updated review of interactions of statins with antibacterial and antifungal agents", 2017, Journal of Translational Science, 3(3), pp. 1-4. (doi: 10.15761/JTS.1000181) (Year: 2017).*
James K. Liao, "Isoprenoids as mediators of the biological effects of statins", 2002, J Clin Invest., 110(3), pp. 285-288. (doi.org/10.1172/JCI16421) (Year: 2002).*
Verhulst et al., "Inhibitors of HMG-CoA Reductase Reduce Receptor-mediated Endocytosis in Human Kidney Proximal Tubular Cells", 2004, J. Am. Soc. Nephrol., 15(9), pp. 2249-2257. (Year: 2004).*
Olyaei et. al., "The Efficacy and Safety of the 3-Hydroxy-3-methylglutaryl-CoA Reductase Inhibitors in Chronic Kidney Disease, Dialysis, and Transplant Patients", 2011, Clin. J. Am. Soc. Nephrol., 6(3), pp. 664-678. (doi: 10.2215/CJN.09091010) (Year: 2011).*
Wang et al., "Potential role of coenzyme Q10 in facilitating recovery from statin-induced rhabdomyolysis", 2015, Internal Medicine Journal, 45(4), pp. 451-453. (doi:10.1111/imj.12712) (Year: 2015).*
Roman V. Hrab et al., "Prevention of fluvastatin-induced toxicity, mortality, and cardiac myopathy in pregnant rats by mevalonic acid supplementation," Teratology, 50(1), 19-26 (1994).

(Continued)

*Primary Examiner* — My-Chau T. Tran
(74) *Attorney, Agent, or Firm* — McDonnell Boehnen Hulbert & Berghoff LLP

(57) ABSTRACT

The present disclosure relates to a pharmaceutical composition for preventing or treating statin-induced adverse effects or a pharmaceutical composition for co-administration with statin, the pharmaceutical composition containing, as an active ingredient, at least one selected from the group consisting of an isoprenoid-based compound, zaragozic acid, terbinafine, and ketoconazole. The pharmaceutical composition according to the present disclosure may prevent and/or treat adverse statin effects that can be induced by statin, that is, can be induced at any time by oxisterols present at abnormal levels in the body. The pharmaceutical composition can not only treat but also prevent the adverse effects of various statin therapeutics whose use has recently increased rapidly, and thus it is expected that the pharmaceutical composition can be widely used for various diseases and the utilization thereof can further be increased.

12 Claims, 18 Drawing Sheets

Specification includes a Sequence Listing.

(56) References Cited

OTHER PUBLICATIONS

Graveline, Duane. "Adverse Effects of statin drugs: a physician patient's perspective." J Am Phys Surg 20 (2015): 7-11.
Kojro, Elzbieta et al., "Statins and the squalene synthase inhibitor zaragozic acid stimulate the non-amyloidogenic pathway of amyloid-β protein precursor processing by suppression of cholesterol synthesis." Journal of Alzheimer's Disease 20, No. 4 (2010): 1215-1231.
International Search Report, Application No. PCT/KR2018/013307, dated Apr. 12, 2019, 3 pages.

\* cited by examiner

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
caggatgcag cacagaatgt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ctttgcatgc tccttgaaca                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gcacagtcaa ggccgagaat                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gccttctcca tggtggtgaa                                              20
```

PHARMACEUTICAL COMPOSITION FOR PREVENTING OR TREATING ADVERSE DRUG REACTIONS BY STATIN

CROSS-REFERENCE TO RELATED APPLICATIONS

This application is a U.S. National Stage application of International Patent Application PCT/KR2018/013307, filed Nov. 5, 2018, which claims the benefit of priority of Korean Patent Application no. 10-2017-0146515, filed Nov. 6, 2017.
[REFERENCE TO AN ELECTRONIC SEQUENCE LISTING]
The instant application contains a Sequence Listing which has been submitted electronically as a text file in ASCII format and is hereby incorporated by reference in its entirety. The name of the ASCII text file is "20-747-WO-US_Sequence-Listing_ST25.txt", was created on Dec. 6, 2021, and is 2,000 bytes in size.

TECHNICAL FIELD

The present disclosure relates to a pharmaceutical composition for preventing or treating statin-induced adverse drug reactions.

BACKGROUND ART

Statin, a cholesterol synthesis inhibitor, is a generic term for hydroxymethylglutaryl-CoA reductase (HMG-CoA reductase) which is a rate-limiting enzyme in the cholesterol synthesis pathway, and a variety of statins have the same basic structure. These compounds have a molecular structure similar to that of HMG-CoA which is a substrate for HMG-CoA reductase, and they may inhibit the conversion of HMG-CoA to mevalonic acid by competitive inhibition, thereby lowering total cholesterol levels and low-density lipoprotein (LDL) levels. For this reason, these compounds have been widely used as therapeutic agents for hyperlipidemia, hypercholesterolemia, hypertension, angina pectoris, and the like. In addition, they are used as primary drugs of choice in the prevention and treatment of heart diseases caused by coronary sclerosis such as angina pectoris and myocardial infarction. Currently, these statins are generalized drugs that are taken by more than 30 million people a day in the world.

A variety of adverse drug reactions (adverse effects) have recently been reported in connection with these statins, and typically include erectile dysfunction, interstitial lung disease, muscle cell damage, insomnia, hypomnesis, gastrointestinal disorders, muscle pain, rhabdomyolysis, etc. (Korean Patent Application Laid-Open Publication No. 10-2011-0136687). According to the experiment published in Journal of the American College of Cardiology on January 2010, it was reported that a follow-up of about 300 adults diagnosed with heart failure, which was conducted for an average of 3.7 years, indicated that people, who did take statin drugs and had low levels of low density lipoprotein (LDL), had the highest morality rate. In addition, in clinical trials conducted in Korea, adverse reactions were observed in 197 (22.2%) of 886 cases administered with Pitarotin Tab (Pitavastatin calcium) (see "Druginfo").

As such, there is an urgent need for a method for lowering the adverse effects of statin drugs effective for treating cholesterol-related diseases and/or cardiovascular diseases, or a drug capable of preventing or treating the adverse effects. Accordingly, the present inventors have conducted studies not only on the causes of statin-induced adverse drug reactions, but also on a method capable of preventing and/or treating the statin-induced adverse drug reactions, thereby completing the present disclosure.

DISCLOSURE

Technical Problem

The present disclosure has been made in order to solve the above-described problems occurring in the prior art, and an object of the present disclosure is to provide a pharmaceutical composition for preventing or treating statin-induced adverse drug reactions, the pharmaceutical composition containing, as an active ingredient, at least one selected from the group consisting of an isoprenoid-based compound, zaragozic acid, terbinafine, and ketoconazole.

Another object of the present disclosure is to provide a pharmaceutical composition for co-administration with statin, the pharmaceutical composition containing, as an active ingredient, at least one selected from the group consisting of an isoprenoid-based compound, zaragozic acid, terbinafine, and ketoconazole.

Still another object of the present disclosure is to provide a method for preventing or treating statin-induced adverse drug reactions, the method including administering to a subject in need thereof a pharmaceutically effective amount of at least one selected from the group consisting of an isoprenoid-based compound, zaragozic acid, terbinafine, and ketoconazole.

However, technical problems to be solved by the present disclosure are not limited to the above-mentioned problems, and other problems which are not mentioned will be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present disclosure. However, certain embodiments may be practiced without one or more of these specific details, or in combination with other known methods and configurations. In other instances, known processes and preparation techniques have not been described in particular detail in order not to unnecessarily obscure the present disclosure. Reference throughout this specification to "one embodiment" or "an embodiment" means that a particular feature, configuration, composition, or characteristic described in connection with the embodiment is included in at least one embodiment of the present disclosure. Thus, the appearances of the phrase "in one embodiment" or "an embodiment" in various places throughout this specification are not necessarily referring to the same embodiment of the present disclosure. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present disclosure pertains.

In the present specification, "adverse drug reactions" refers, in a broad sense, to unwanted reactions induced by a specific drug, and preferably refers to adverse effects caused by a drug. In the present specification, the adverse drug reactions refer to any adverse effects that may be induced by a statin which is a cholesterol synthesis inhibitor. Preferably, the adverse drug reactions refer to adverse statin effects induced by increased concentrations of oxysterols in vivo. More preferably, the adverse drug reactions refer to adverse effects caused by damage to cells such as kidney tubule cells, pancreatic cells or nerve cells, or any adverse effects that may be induced by statin, but are not limited thereto.

The statin is administered into the body at a low concentration so that HMG-CoA reductase in the mevalonate pathway can be competitively inhibited. Here, in an environment in which oxysterols that are abnormally increased compared to those in normal people due to inflammation or the like are not present, the activity of sterol regulatory element-binding protein 2 (SREBP2) may increase, and ultimately, the synthesis of a proper amount of cholesterol required in the body, and protein prenylation which is very important for protein-protein interaction, may occur normally. On the other hand, where oxysterols in the body are abnormally increased compared to those in normal people due to inflammation or the like, the activity of SREBP2, which is activated when the mevalonate pathway is inhibited by statin, is inhibited, and hence normal protein prenylation may not occur, and damage to various cells may be induced by this phenomenon.

In the present specification, "preventing" refers, in a broad sense, to preventing the occurrence of statin-induced adverse effects, and preferably includes both primary prevention that is performed in advance before the occurrence of statin-induced adverse effects, and secondary prevention that is performed to detect the occurrence of statin-induced adverse effects early and treat them in a timely manner. However, preventing is not limited thereto as long as it is any procedure and/or activity taken prior to the occurrence of statin-induced adverse effects.

In the present specification, "treating" refers, in a broad sense, to a procedure taken against statin-induced adverse effects, and is not limited as long as it is any procedure and/or activity for treating, curing, ameliorating or reducing statin-induced adverse effects.

The present disclosure provides a pharmaceutical composition for preventing or treating statin-induced adverse drug reactions, the pharmaceutical composition containing, as an active ingredient, at least one selected from the group consisting of an isoprenoid-based compound, zaragozic acid, terbinafine, and ketoconazole.

The present disclosure also provides a pharmaceutical composition for co-administration with statin, the pharmaceutical composition containing, as an active ingredient, at least one selected from the group consisting of an isoprenoid-based compound, zaragozic acid, terbinafine, and ketoconazole.

The present disclosure also provides a method for preventing or treating statin-induced adverse drug reactions, the method including administering to a subject in need thereof a pharmaceutically effective amount of at least one selected from the group consisting of an isoprenoid-based compound, zaragozic acid, terbinafine, and ketoconazole.

The active ingredient that is contained in the pharmaceutical composition of the present disclosure includes a compound that may function to suppress protein prenylation from being completely blocked when a statin is administered in a state in which oxysterols that abnormally increased compared to those in normal people due to inflammation or the like are present in the body, that is, when statin-induced adverse drug reactions occur. Specifically, the active ingredient may include any compound that can activate the mevalonate pathway at a normal level so that protein prenylation may occur.

In one embodiment of the present disclosure, the isoprenoid-based compound may be farnesyl pyrophosphate, mevalonate, isopentenyl pyrophosphate, geranylgeranyl pyrophosphate, or the like, but is not limited thereto as long as it is a compound that is involved in protein prenylation.

In another embodiment of the present disclosure, the statin may preferably be atorvastatin, rosuvastatin, simvastatin, pitavastatin, pravastatin, fluvastatin, lovastatin, cerivastatin, mevastatin, or the like, but is not limited thereto as long as it is a cholesterol synthesis inhibitor.

The statin may be administered at a defined daily dose that is generally used for treatment. The defined daily dose may be 0.5 mg to 1,500 mg, preferably 0.5 mg to 1,000 mg, more preferably 0.5 mg to 100 mg, 0.5 mg to 80 mg, or 0.5 mg to 50 mg, but is not limited thereto as long as it is an approved defined daily dose. In addition, the statin may be administered together with an ezetimibe formulation, a niacin extended-release formulation, an amlodipine formulation, or the like, but the formulation is not limited thereto as long as it is generally administered together with statin.

In still another embodiment of the present disclosure, the adverse drug reactions (adverse effects) are caused by increased in vivo concentrations of oxysterols. Preferably, the adverse drug reactions are caused by cell damage to such as kidney tubule cells, nerve cells or pancreatic cells. More preferably, the adverse drug effects may be adverse drug effects not only in diseases such as cognitive dysfunction, dementia, acute renal failure, acute tubular necrosis injury, ischemic reperfusion injury, Parkinson's disease, Alzheimer's disease, Huntington's syndrome, stroke, spinal nerve damage, diabetes, and hyperlipidemia, but also in common symptoms such as cold and fatigue, but are not limited thereto as long as they are statin-induced adverse drug reactions that may be caused by increased concentrations of oxysterols.

In yet another embodiment of the present disclosure, the oxysterols may preferably be 25-hydroxycholesterol, 7-ketocholesterol, cholesterol 5,6-epoxide, 24-hydroxycholesterol, 27-hydroxycholesterol, 4β-hydroxycholesterol, 19-hydroxycholesterol, 7β-hydroxycholesterol, 7α-hydroxycholesterol, 26-hydroxycholesterol, 7-oxysterol, cholestan-3β, 5α, 6β-triol, 5,6-chlorohydrins, 24,25-epoxysterols, 32-oxysterol, 4-hydroxysterol, 19-hydroxysterol, 15-oxysterol, 22-hydroxysterol, 20-hydroxysterol, 5α,6α-epoxycholesterol, 5β,6β-epoxycholesterol, and 5α,6β-dihydroxycholesterol, or oxysterols that are produced in vivo by lipopolysaccharides, but are not limited as long as they are oxysterol species that may be produced or administered in vivo.

In the present disclosure, the increased in vivo concentrations of oxysterols may be 0.5 ng/mL to 10 μg/mL, preferably 0.5 ng/mL to 5 μg/mL, more preferably 1 ng/mL to 2.5 μg/mL, but are not limited as long as they are concentrations higher than the concentrations of oxysterols that are usually produced in the bodies of individual patients.

In the present disclosure, the pharmaceutical composition may be in the form of capsule, tablet, granule, injection, ointment, powder or beverage, and the pharmaceutical composition may be for administration to humans. For use, the pharmaceutical composition may be formulated in the form of, but not limited to, oral preparations, such as powders, granules, capsules, tablets, and aqueous suspensions, as well as external preparations, suppositories, and sterile injectable solutions, according to conventional methods. The pharmaceutical composition of the present disclosure may contain pharmaceutically acceptable carriers. Pharmaceutically acceptable carriers that may be used for oral administration include binders, lubricants, disintegrants, excipients, solubilizers, dispersants, stabilizers, suspending agents, pigments, flavorings, and the like, and pharmaceutically acceptable carriers that may be used for injection include buffers, preservatives, analgesics, solubilizers, isotonic agents, stabilizers, and the like. Pharmaceutically acceptable carriers that may be used for topical administration include bases, excipients, lubricants, preservatives, and the like. The formulation of the pharmaceutical composition of the present disclosure may be prepared in various ways by mixing with pharmaceutically acceptable carriers as described above. For example, for oral administration, the pharmaceutical composition may be prepared in the form of tablets, troches, capsules, elixir, suspensions, syrups or wafers, and for injection, the pharmaceutical composition may be presented in unit dose ampoules, multi-dose containers or the like. In addition, the pharmaceutical composition may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present disclosure may further contain a filler, an anticoagulant, a lubricant, a wetting agent, a fragrance, an emulsifier, a preservative, or the like.

The routes of administration of the pharmaceutical composition according to the present disclosure include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred. As used herein, the term "parenteral" includes subcutaneous, transdermal, intravenous, intramuscular, intra-articular, intra-synovial, intrasternal, intradural, intra-lesional and intra-cranial injection Or infusion techniques. The pharmaceutical composition of the present disclosure may also be formulated as suppositories for intrarectal administration.

The pharmaceutical composition and the prevention or treatment method of the present disclosure may vary depending on various factors, including the activity of a specific compound used in the prevention or treatment method, the patient's age, body weight, general health, sex, diet, the period of administration, the route of administration, excretion rate, the drug content, and the severity of a specific disease to be prevented or treated. The dose of the pharmaceutical composition may vary depending on the patient's condition and body weight, the severity of the disease, the form of drug, and the route and period of administration, but may be suitably selected by a person skilled in the art and may be 0.0001 mg/kg/day to 50 mg/kg/day or 0.001 mg/kg/day to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

Advantageous Effects

The pharmaceutical composition, the pharmaceutical composition for co-administration with statin and the method of treating by administering the same according to the present disclosure may prevent and/or treat adverse statin effects that can be induced by statin, that is, can be induced at any time by oxisterols present at abnormal levels in the body. They can not only treat but also prevent the adverse effects of statin therapeutics whose use has recently increased rapidly, and thus it is expected that they can be widely used for various diseases and the utilization thereof can further be increased.

BEST MODE

In accordance with an embodiment of the present disclosure, there is provided a pharmaceutical composition for preventing or treating statin-induced adverse drug reactions, the pharmaceutical composition containing, as an active ingredient, at least one selected from the group consisting of an isoprenoid-based compound, zaragozic acid, terbinafine, and ketoconazole.

In accordance with another embodiment of the present disclosure, there is provided a pharmaceutical composition for co-administration with statin, the pharmaceutical composition containing, as an active ingredient, at least one selected from the group consisting of an isoprenoid-based compound, zaragozic acid, terbinafine, and ketoconazole.

In accordance with still another embodiment of the present disclosure, there is provided a method for preventing or treating statin-induced adverse drug reactions, the method including administering to a subject in need thereof a pharmaceutically effective amount of at least one selected from the group consisting of an isoprenoid-based compound, zaragozic acid, terbinafine, and ketoconazole.

MODE FOR INVENTION

Hereinafter, the present disclosure will be described in more detail with reference to examples. It will be obvious to those skilled in the art that these examples are merely to illustrate the present disclosure in more detail and the scope of the present disclosure according to the gist of the present disclosure is not limited to these examples.

EXAMPLES

Example 1: Analysis of Relationship Between Statins and Oxysterols 1.1. Analysis of Relationship Between Various Types of Statins and Oxysterol To analyze the relationship between statins and oxysterols, the human kidney tubule cell line HK-2 (human kidney-2 cell line; ATCC CRL-2190™) was seeded into a 24-well plate at a density of $1 \times 10^5$ per well. In addition, each well was treated with 5 µM of atorvastatin or 1 µM of fluvastatin, and 0 or 0.1 µg/mL of 25-hydroxycholesterol (25-HC), a kind of oxysterol, was added to each well. Subsequently, the cells were cultured in an incubator at 37° C. under 5% $CO_2$ for 72 hours, and then the degree of cell death in each well was analyzed using an LDH assay kit (Takara, Cat #. MK401). The results are shown in FIGS. 1 and 2.

Figure 1:
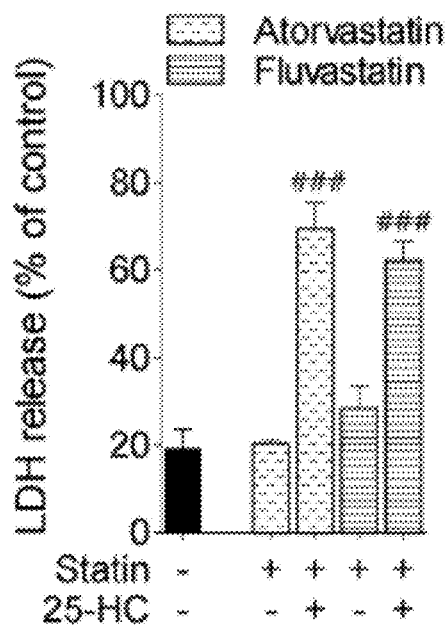
FIGS. 1 and 2 show the results of analyzing the relationship between various types of statins and oxysterol according to an Example of the present disclosure.
Figure 2:
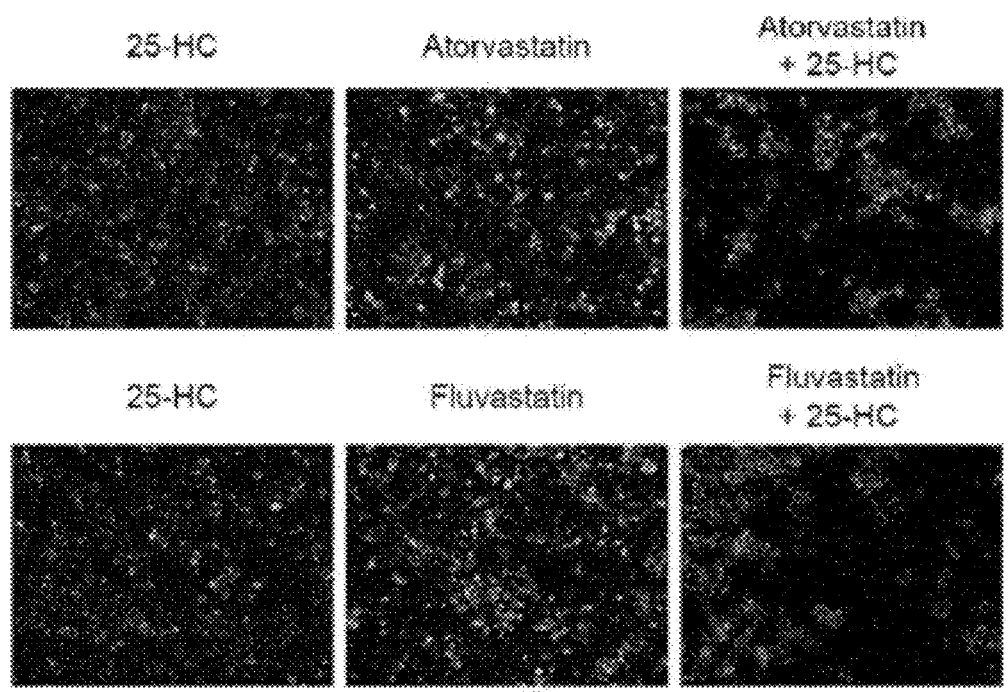

As shown in FIGS. 1 and 2, it was confirmed that when the cells were treated with the statin or the oxysterol alone, no cell death was induced, but when the statin and the oxysterol were co-administered to the cells, rapid cell death was induced. From these results, it was confirmed that, regardless of the type of statin, significant cell death in the kidney tubule cell line was induced even when the oxysterol was present at a concentration of 0.1 µg/mL, which corresponds to a low concentration at which no toxicity occurs. This suggests that when oxysterol is present in vivo, protein prenylation may be inhibited regardless of the dose of statin, and hence adverse effects such as cell death may occur.

1.2. Analysis of Relationship Between Various Types of Oxysterols and Statin

In order to examine whether the same results appear even in the presence of various types of oxysteols, an experiment was performed in the same manner as Example 1.1. As statin, 5 µM of atorvastatin was used, and as oxysterols, 0.1 µg/mL of 25-hydroxycholesterol, 7-ketocholesterol, cholesterol 5,6-epoxide, 24-hydroxycholesterol and 27-hydroxycholesterol were used. The results are shown in FIG. 3.

Figure 3:
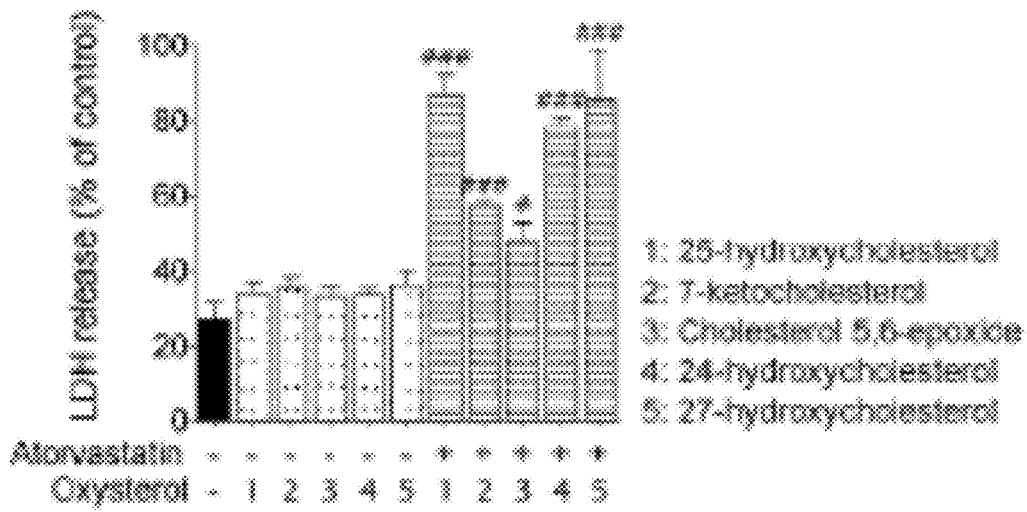
FIG. 3 shows the results of analyzing the relationship between various types of oxysterols and statin according to an Example of the present disclosure.

As shown in FIG. 3, it was confirmed that, in the cell line to which the oxysterols were administered alone, no cell death occurred, but in all the experimental groups to which the statin and each of the oxysterols were co-administered, cell death was induced. From these results, it was confirmed that, regardless of the type of oxysterol, significant cell death was induced in the kidney tubule cell line when the statin was present even at a low concentration at which no toxicity occurs. This suggests that statin-induced adverse effects may occur in the presence of oxysterols in vivo.

From the above results, it was confirmed that strong cytotoxicity to the kidney tubule cells was induced by co-administration of various types of oxystreols and statins. Through this, it was confirmed that at a low concentration of the oxysterol or a low concentration of the statin, no cell toxicity was induced, but when the oxysterol and the statin were co-administered, strong cytotoxicity to the kidney tubule cells could be induced even at low concentrations of the oxysterol and the statin. In addition, it could be confirmed that when the oxysterol is present at high concentration in vivo, administration of the statin for treatment can cause adverse effects such as acute renal failure (acute kidney injury).

Example 2: Evaluation of Effect of Isoprenoid-Based Compounds on Reduction of Adverse Effects In order to examine whether isoprenoid-based compounds can reduce adverse effects which are induced by co-administration of oxysterol and statin, the cell line was treated with oxysterol (0.1 µg/mL of 25-hydroxycholestyerol) and statin (5 µM of atorvastatin) in the same manner as Example 1.1, and treated with 10 µM of farnesyl pyrophosphate, 200 µM of mevalonate or 10 µM of geranylgeranyl pyrophosphate, which is an isoprenoid-based compound. In addition, the cells were treated with 10 µg/mL of 25-hydroxycholesterol and 1 µM of zaragozic acid. The results are shown in FIGS. 4 to 6.

Figure 4:
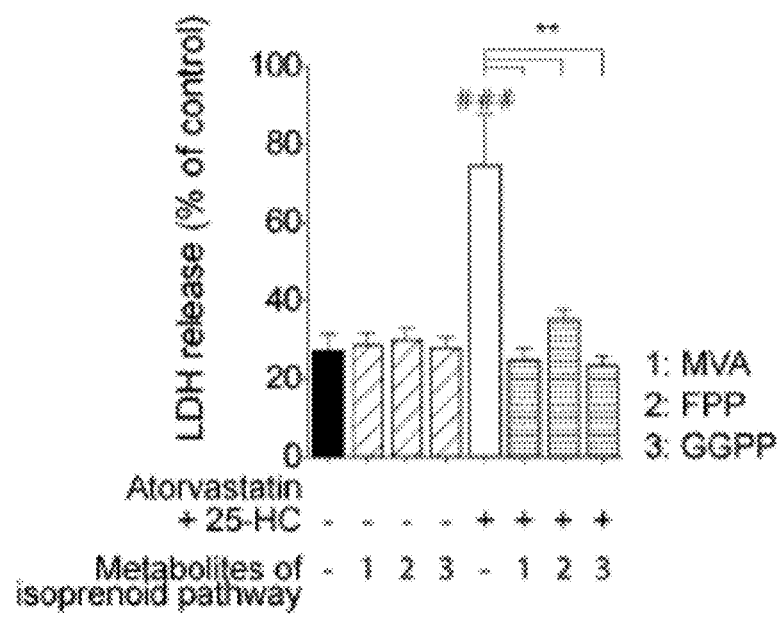
FIGS. 4 to 6 show the results of evaluating the preventive and therapeutic effects of isoprenoid-based compounds on the adverse statin effects of co-administration of statin and oxysterol according to an Example of the present disclosure.
Figure 5:
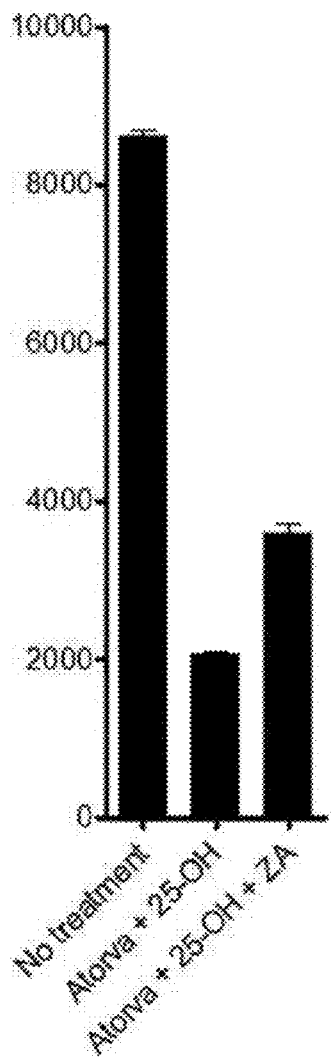
Figure 6:
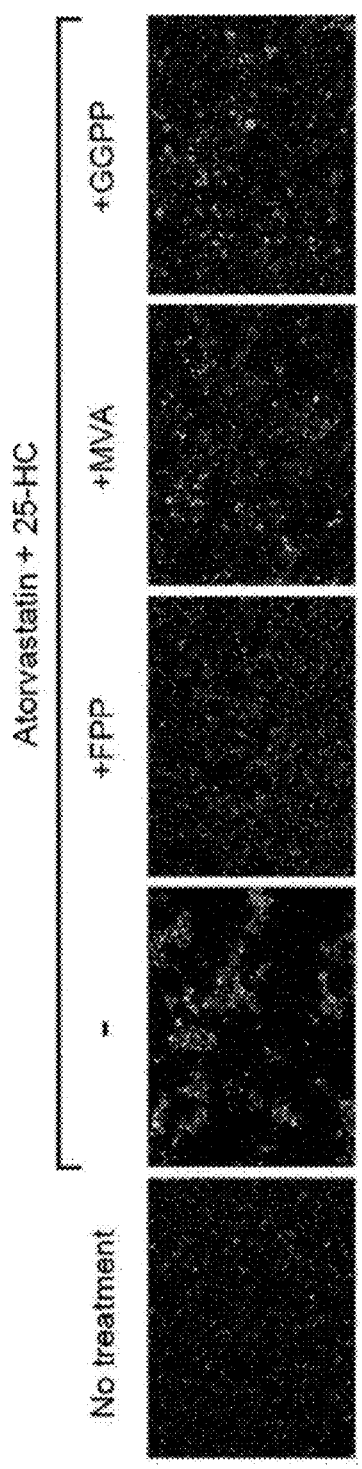

As shown in FIGS. 4 to 6, it was confirmed that cell death induced by co-administration of the oxysterol and the statin was inhibited by the isoprenoid-based compound. In addition, it was confirmed that even when the cells were treated with zaragozic acid, the adverse effects were reduced to some degrees, and thus the viability of the cells increased. From these results, it can be confirmed that, regarding adverse effects induced by statin administration, the isoprenoid-based compound or the zaragozic acid allows protein phenylation to be induced by the mevalonate pathway, and when the isoprenoid-based compound or the zaragozic acid is co-administered with statin, it can prevent adverse effects, which can be induced by statin administration when the in vivo concentrations of oxysterols are outside normal levels, or reduce the extent of the adverse effects. Furthermore, it could be confirmed that the adverse effects that occurred could also be treated.

Example 3: Analysis of Relationship Between Adverse Effects of Co-Administration of Statin with Oxysterol and Tissue In order to examine whether the adverse effects of co-administration of statin with oxysterol show different results depending on tissues in vivo, in addition to the kidney tubule cell line HK-2, primary renal tubule cells (ATCC® PCS-400-010™), renal mesangial cells (ScienCell Cat. # #4200), primary hepatocytes (cultured after isolation from C57BL6/J mice), and pancreatic Ins-1e cells (ThermoFisher Scientific) were treated with oxysterol (0.1 μg/mL of 25-hydroxycholesterol) and statin in the same manner as Example 1.1, and the degree of cell death was analyzed. Primary neurons were obtained by euthanizing the mother mouse and then collecting brain tissue from the fetal head in the womb. After removing the arachnoid and pia mater from the obtained brain tissue, the hippocampus was isolated and transferred to DM media (dissection media; 490 mL of HBSS, 5 mL of HEPES, and 5 mL of penicillin/streptomycin), and then the cerebral cortex was isolated therefrom. Generally, the cerebral cortex was isolated from two mouse fetuses, and the hippocampus was used in an amount isolated from all the fetuses isolated from one mother mouse. Each isolated hippocampus or cerebral cortex was placed in a 15-mL tube, and washed and disrupted with trypsin and DM media, and the cells were collected. For image acquisition, the collected cells were seeded in PM media (plating media; 485 mL of Neurobasal media, 10 mL of B-27 supplement, and 5 mL of 100 X glutamax) at a concentration of $1 \times 10^5$ to $5 \times 10^5$ cells/mL, and for experimental use, the cells was seeded in PM media at a concentration of $5 \times 10^5$ to $1 \times 10^6$ cells/mL. Then, the cells were cultured for 2 weeks and used in the experiment. The results are shown in FIGS. 7 and 8.

Figure 7:
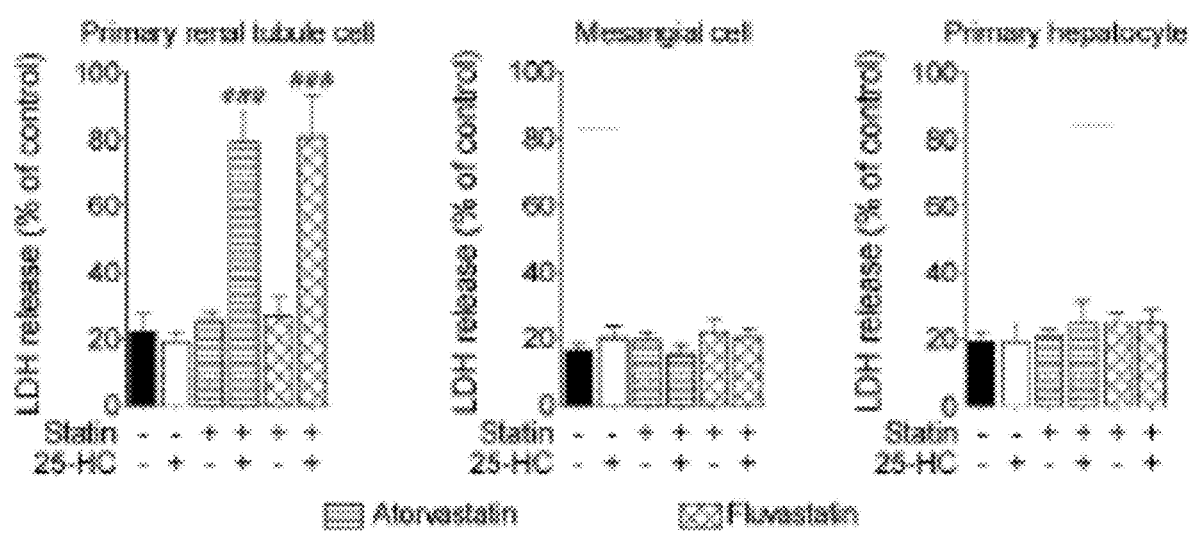
FIG. 7 shows the results of analyzing the difference in adverse statin effects between tissues according to an Example of the present disclosure.
Figure 8:
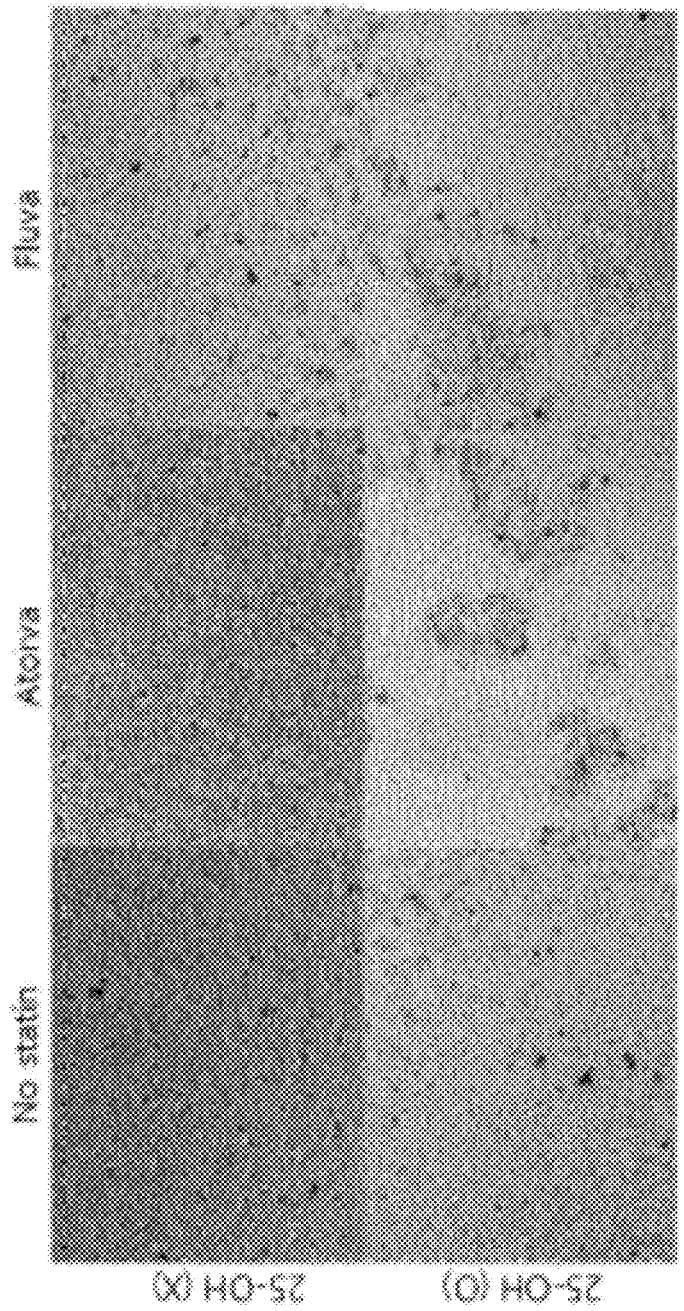
FIG. 8 shows the results of analyzing the difference in adverse statin effects on pancreas according to an Example of the present disclosure.

As shown in FIGS. 7 and 8, it was confirmed that, in the renal mesangial cells and the primary hepatocytes, co-administration of the statin and the oxysterol showed no cytotoxicity, whereas, in the primary renal tubule cells and the pancreatic Ins-1e cells, significant cell death was induced by co-administration of the statin and the oxysterol. In addition, it was confirmed that when each of the statin or the oxysterol was administered alone, no cell death was observed even in primary nerve cells, but when the statin and the oxysterol were co-administered to the primary nerve cells, cell death significantly increased. From the above results, it was confirmed that cytotoxicity caused by co-administration of the oxysterol and the statin occurred in a cell-specific manner. This suggests that adverse effects caused by administration of statin in a state in which the concentration of oxysterols in vivo is high occur in a tissue-specific manner. In particular, it can be confirmed that the adverse effects cause damage to kidney tubule cells, nerve cells and pancreatic cells.

Figure 9:
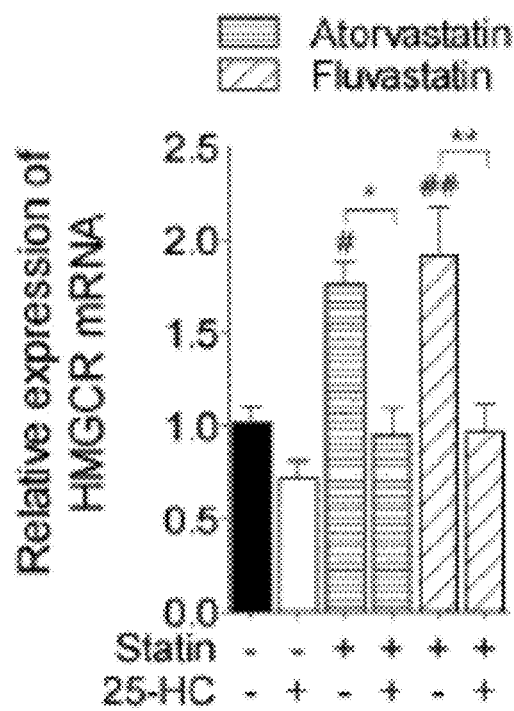
FIG. 9 shows the results of real-time polymerase chain reaction performed to analyze the mechanism of adverse effects of co-administration of statin and oxysterol according to an Example of the present disclosure.
Figure 10:
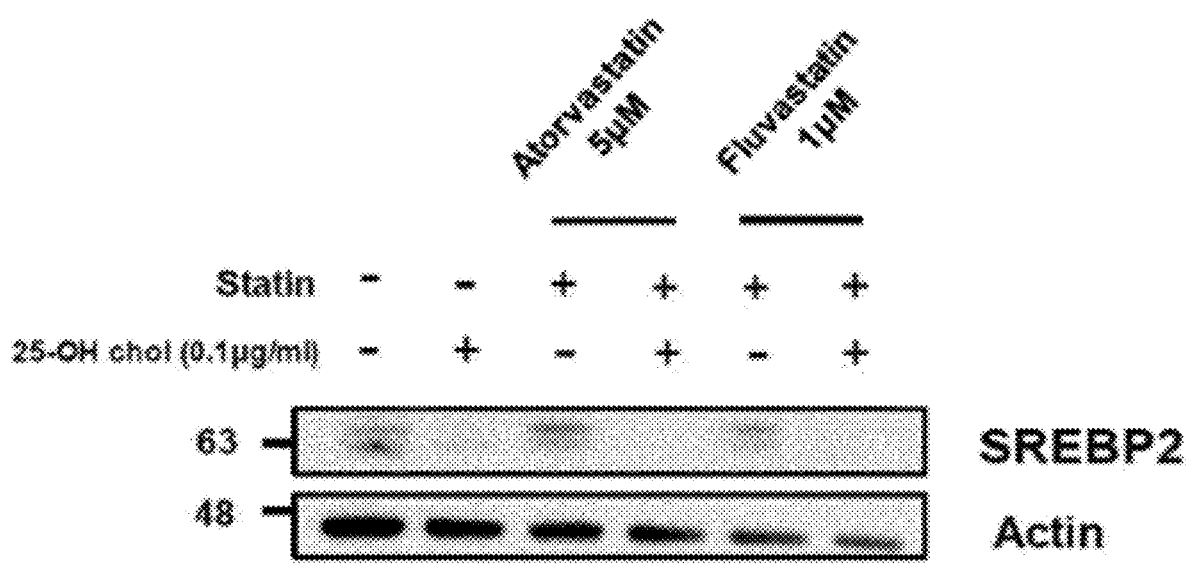
FIG. 10 shows the results of Western blotting performed to analyze the mechanism of adverse effects of co-administration of statin and oxysterol according to an Example of the present disclosure.

Example 4: Analysis of Mechanism of Adverse Effects Caused by Co-Administration of Statin and Oxysterol In order to examine the causes of adverse effects induced by co-administration of statin and oxysterol, the HK-2 cell line was seeded into a 24-well plate at a density of $1 \times 10^5$ cells per well. Then, each well was treated with 5 μM of atorvastatin or 1 μM of fluvastatin, and 0.1 μg/mL of 25-hydroxycholesterol was added to each well. Next, the cells were cultured in an incubator at 37° C. under 5% $CO_2$ for 24 hours, and then mRNA was extracted from the cells using an RNA isolation kit (Qiagen). In addition, protein was extracted using a ReadyPrep Protein Extraction kit (Bio-rad). Using the extracted mRNA as a template, cDNA was synthesized using a Prime Script RT-PCR kit (Takara). Using the synthesized cDNA, the expression level of HMGCR (3-hydroxy-3-methylglutaryl CoA reductase; HMG-CoA reductase) gene was quantified by real-time polymerase chain reaction. The primer sequences used for the real-time polymerase chain reaction are shown in Table 1 below, and the results of the quantification are shown in FIG. 9. In addition, the extracted protein was analyzed by Western blotting using anti-cleaved SREBP2 (sterol regulatory element binding protein 2) antibody (Abcam), and the results of the analysis are shown in FIG. 10.

TABLE

| Gene | Primer sequence |
|------|-----------------|
| HMG-CoA reductase | Forward: 5'-CAGGATGCAGCACAGAATGT-3'<br>Reverse: 5'-CTTTGCATGCTCCTTGAACA-3' |
| GAPDH | Forward: 5'-GCACAGTCAAGGCCGAGAAT-3'<br>Reverse: 5'-GCCTTCTCCATGGTGGTGAA-3' |

As shown in FIG. 9, it was confirmed that when the cells were treated with a low concentration of the statin, the expression of HMGCR increased, but when the statin and the oxysterol were co-administered to the cells, the expression of HMGCR decreased. From these results, it could be confirmed that when a low concentration of the statin was administered to the cells, the expression of HMGCR was increased by positive feedback, but in the presence of the oxysterol, the positive feedback was inhibited.

In addition, as shown in FIG. 10, it was confirmed that when the cells were treated with a low concentration of the statin, activated SREBP2 increased, but in the presence of the oxysterol, the increase in SREBP2 was inhibited.

From the above results, it could be confirmed that when the cells were treated with a low concentration of the statin, the adverse effects of the statin were reduced by positive feedback, but in the presence of the oxysterol, the positive feedback was inhibited, and hence damage to the cells was induced, and finally, adverse effects on various tissues were induced.

Example 5: Evaluation of Adverse Effects of Co-Administration of Statin and Oxysterol In Vivo In order to examine whether co-administration of statin and oxysterol also induces adverse effects in vivo, 100 mg of statin (atorvastatin or fluvastatin) was added to 1 kg of feed so that the statin could be administered at a dose of about 20 mg to 30 mg per kg of mouse body weight. The mixture was fed to 8-week-old C57BL6/J mice for 14 days. After 14 days, lipopolysaccharide (LPS, SIGMA) was administered intraperitoneally to mice at a lipopolysaccharide dose of 12 mg per kg of mouse body weight so that the concentration of oxysterol in the body reached 5 ng/mL to 5 µg/mL, thereby producing oxysterol in the mouse body (see "J Lipid Res (2009) 50:2258-2264; PNAS (2009) 106: 16764-16769"). 72 hours after administration of the lipopolysaccharide, the mice were euthanized, and then kidney tissue was extracted by performing cardiac perfusion with 4% paraformaldehyde in DPBS (Dulbecco's phosphate-buffered saline). The extracted kidney tissue was subjected to H & E (Hematoxylin & Eosin) staining, PAS (periodic acid-Schiff) staining and immunohistochemistry of neutrophil gelatinase-associated lipocalin (NGAL) that is an early diagnostic marker of acute renal failure, thereby determining whether acute kidney damage and acute renal failure would occur. The results are shown in FIGS. 11 to 16.

Figure 11:
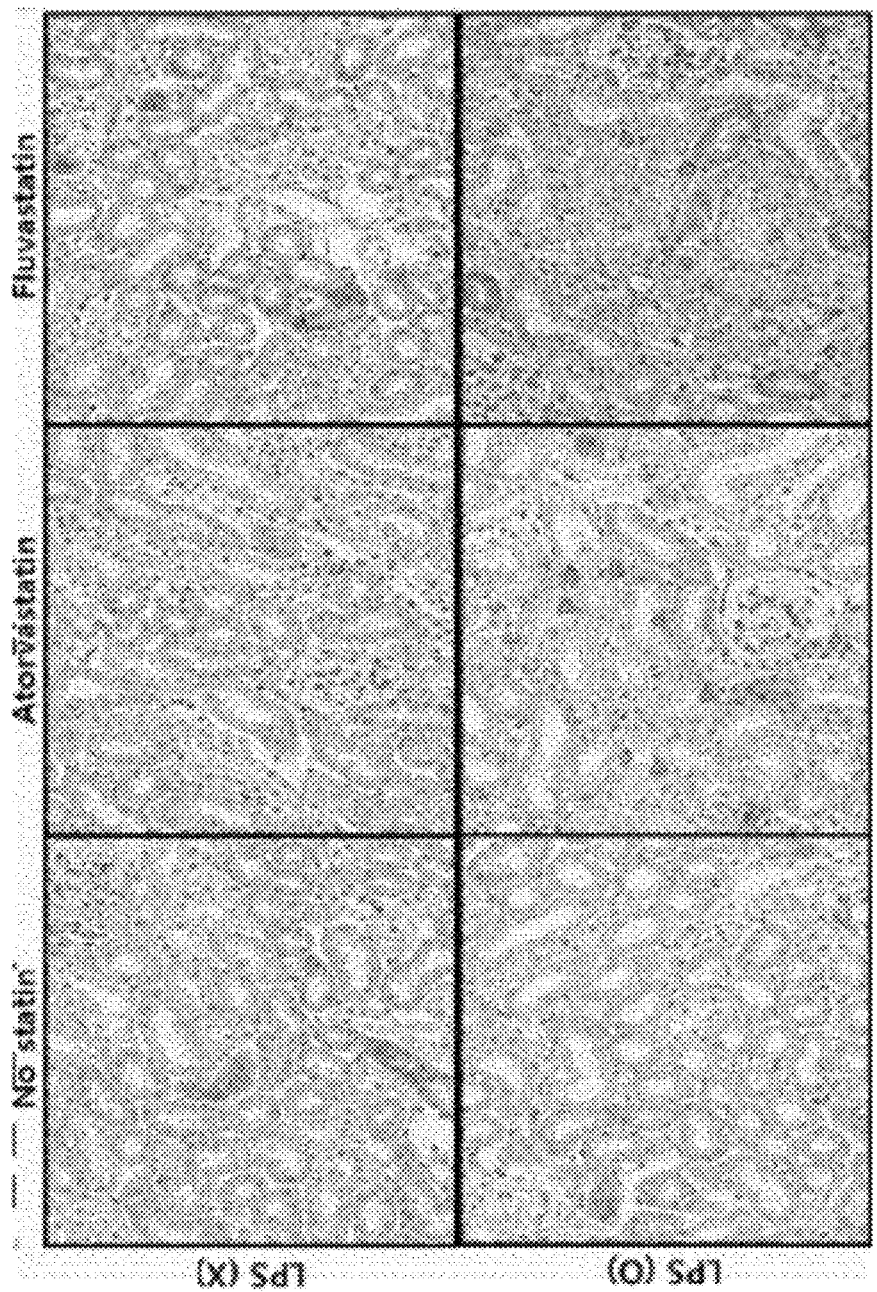
FIG. 11 shows the results of H & E staining performed to analyze adverse statin effects in the presence of oxysterols in vivo according to an Example of the present disclosure.

FIG. 11 shows the results of performing H & E staining. In FIG. 11, the blue arrow indicates the site where a cast was formed, and the blue arrowhead indicates the site where tubule cell vacuolization was induced. As shown in FIG. 11, it was confirmed that when the generation of oxysterol was induced in the experimental group to which the statin was administered, acute renal failure was induced.

Figure 12:
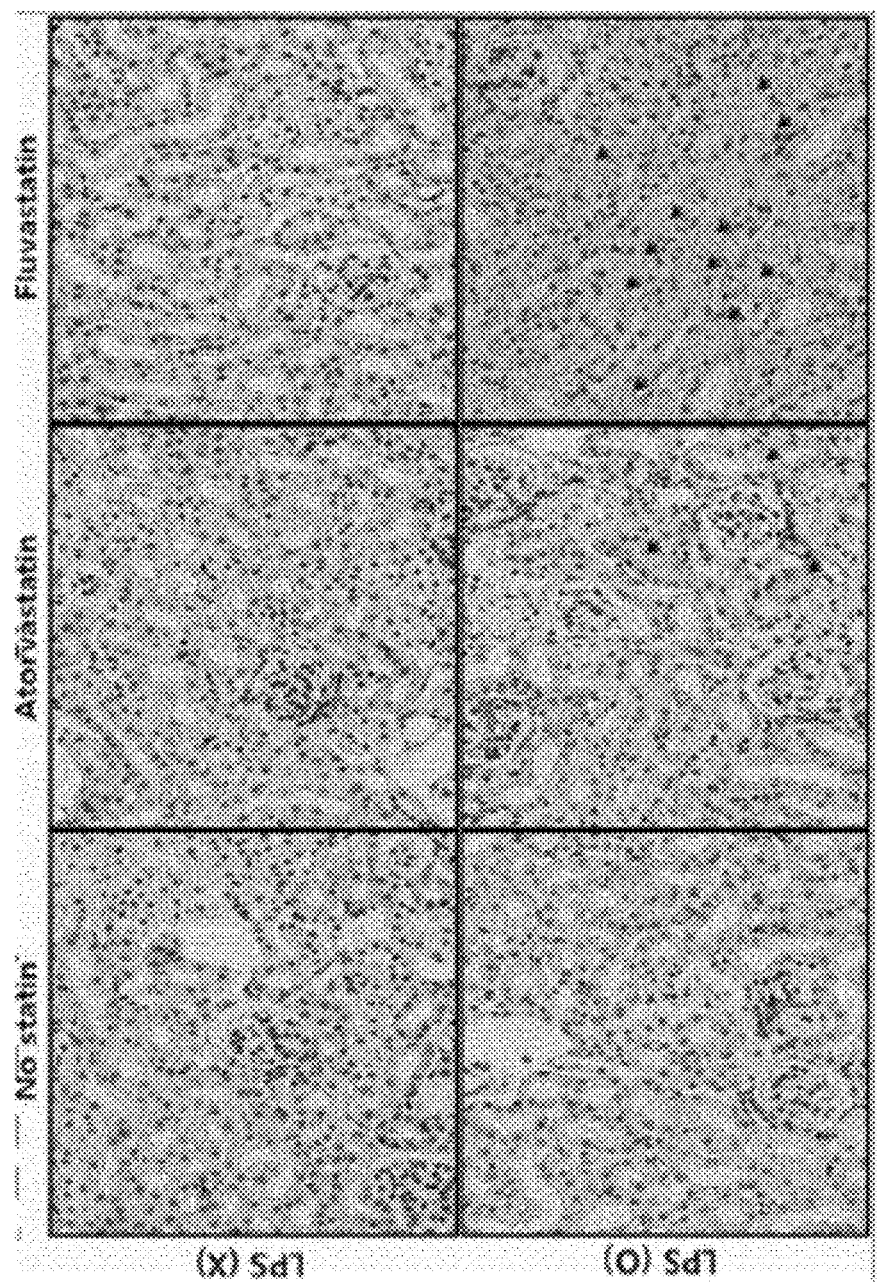
FIG. 12 shows the results of PAS staining performed to analyze adverse statin effects in the presence of oxysterols in vivo according to an Example of the present disclosure.

FIG. 12 shows the results of performing PAS staining. In FIG. 12, the red arrow indicates the site where a cast was formed. As shown in FIG. 12, it was confirmed that when the generation of oxysterol was induced in the experimental group to which the statin was administered, acute renal failure was induced.

Figure 13:
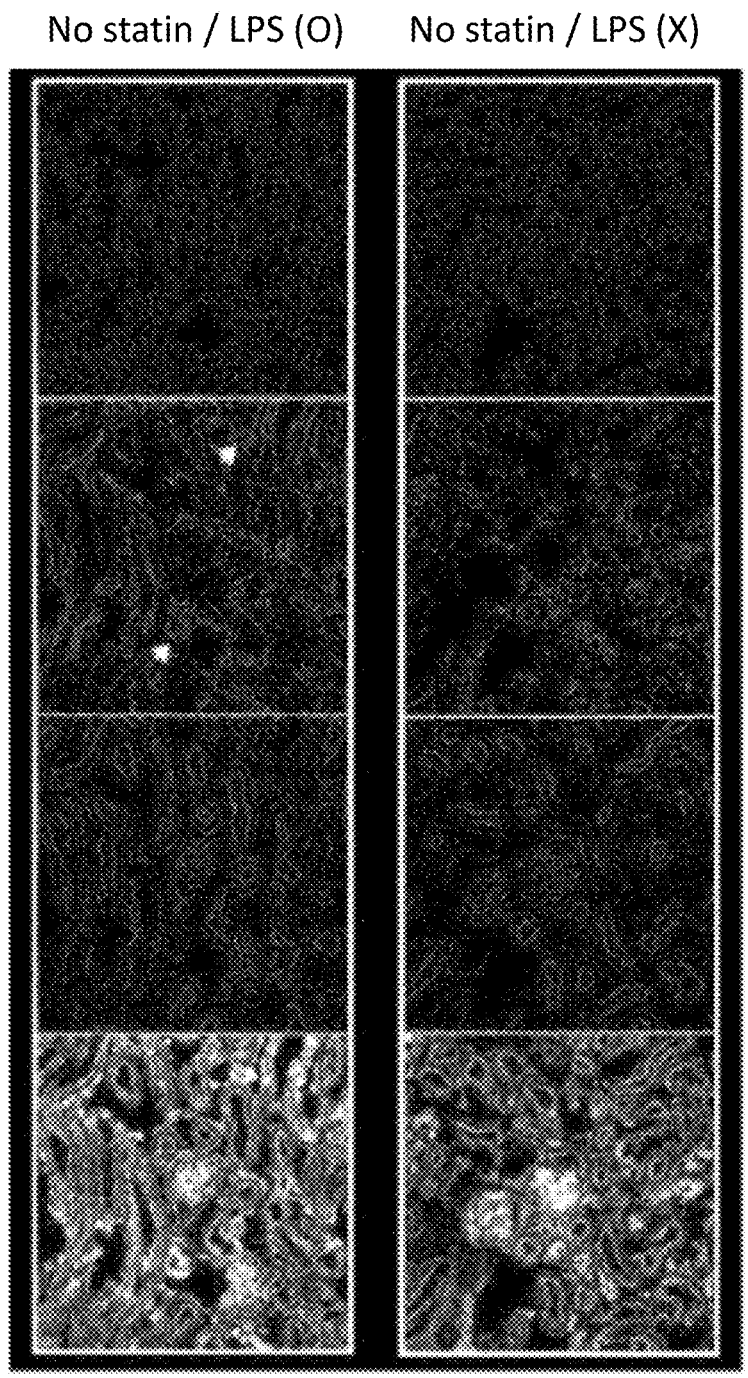
FIG. 13 shows the results of NGAL immunohistochemistry performed to analyze adverse statin effects in the presence of oxysterols in vivo according to an Example of the present disclosure.
Figure 14:
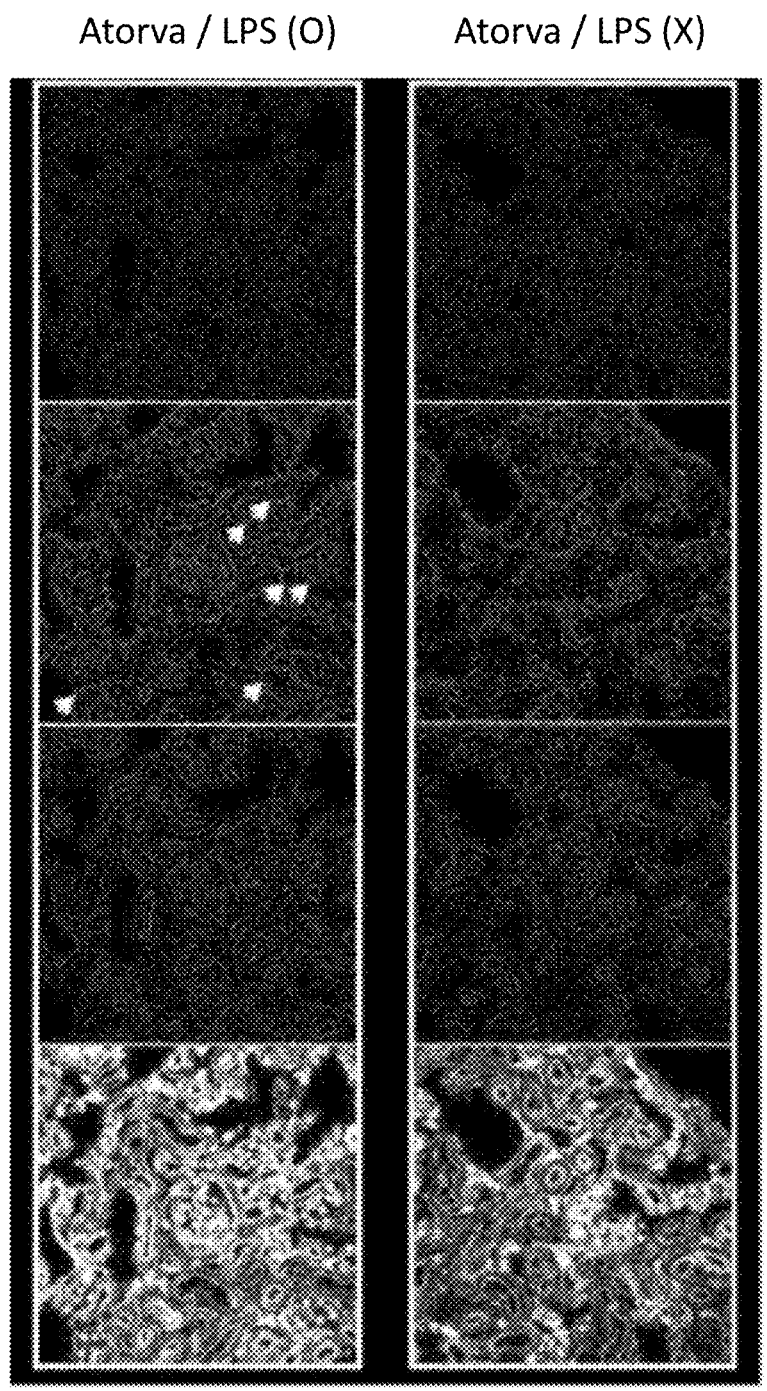
FIG. 14 shows the results of NGAL immunohistochemistry performed to analyze adverse statin effects in the presence of oxysterols in vivo according to an Example of the present disclosure.
Figure 15:
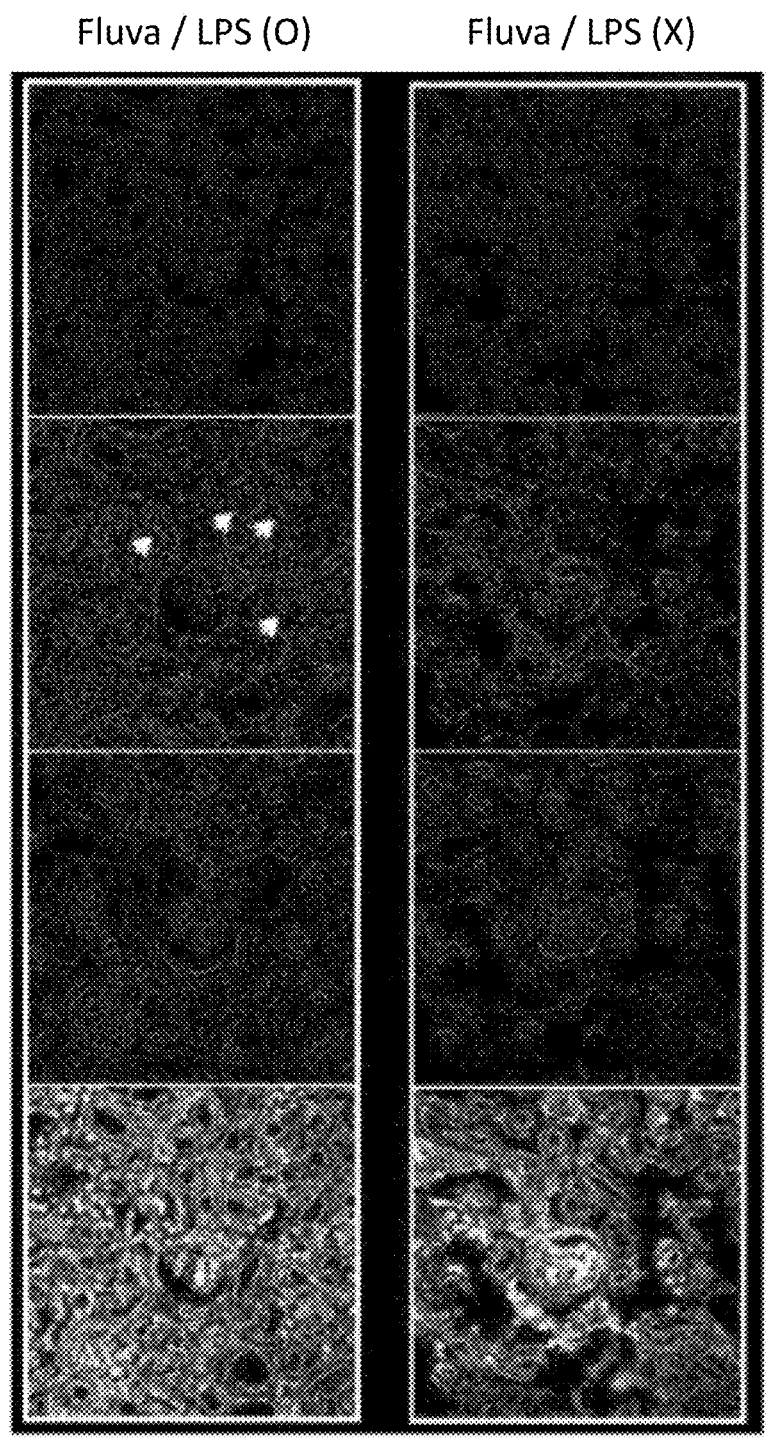
FIG. 15 shows the results of NGAL immunohistochemistry performed to analyze adverse statin effects in the presence of oxysterols in vivo according to an Example of the present disclosure.
Figure 16:
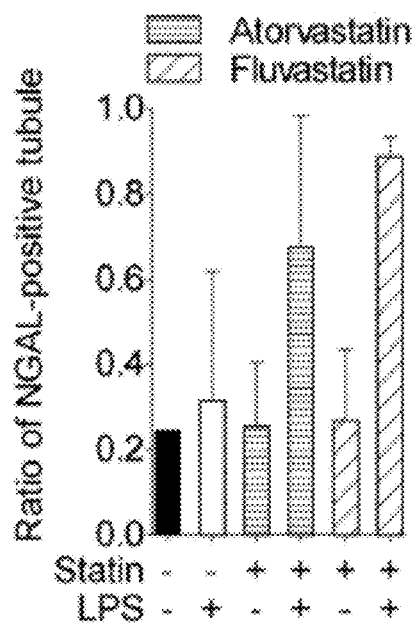
FIG. 16 is a graph showing the results of quantifying the results of NGAL immunohistochemistry according to an Example of the present disclosure.

FIGS. 13 to 15 show the results of performing NGAL immunohistochemistry. In FIGS. 13 to 15, red represents phalloidin indicating the tubule structure, green represents NGAL, and blue represents DAPI indicating the cell nucleus. In addition, FIG. 16 is a graph showing the results of quantifying NGAL staining. As shown in FIGS. 13 to 16, it could be confirmed that only when the generation of oxysterol was induced in the experimental group to which the statin was administered, the expression of NGAL, an early diagnostic marker of acute renal failure, significantly increased.

From the above results, it could be confirmed that statin-induced adverse effects were not induced by administration of a low concentration of the statin in vivo or by the oxysterol alone, but administration of a low concentration of the statin in the presence of the oxysterol could induce rapid damage to the cells, thus inducing adverse effects such as acute renal failure.

Example 6: Evaluation of Effect of Isoprenoid-Based Compound on Reduction of Adverse Effects In Vivo In order to examine whether administration of an isoprenoid-based compound reduces statin-induced adverse effects even in vivo, 100 mg of statin (fluvastatin) was added to 1 kg of feed, and the mixture was fed to 8-week-old C57BL6/J mice for 14 days. Subsequently, mevalonate was administered intraperitoneally to the mice at a dose of 30 mg per kg of mouse body weight for 4 consecutive days, and then lipopolysaccharide (SIGMA) was administered intraperitoneally to mice at a lipopolysaccharide dose of 12 mg per kg of mouse body weight, thereby producing oxysterol in the mouse body. 72 hours after administration of the lipopolysaccharide, the mice were euthanized, and then kidney tissue was extracted by performing cardiac perfusion with 4% paraformaldehyde in DPBS (Dulbecco's phosphate-buffered saline). The extracted kidney tissue was subjected to H & E (Hematoxylin & Eosin) staining, PAS (periodic acid-Schiff) staining and immunohistochemistry of neutrophil gelatinase-associated lipocalin (NGAL) that is an early diagnostic marker of acute renal failure, thereby determining whether acute kidney damage and acute renal failure would occur. In addition, the concentrations of total cholesterol, high-density lipoprotein (HDL) and low-density lipoprotein (LDL) were measured. The results are shown in FIGS. 17 to 23.

Figure 17:
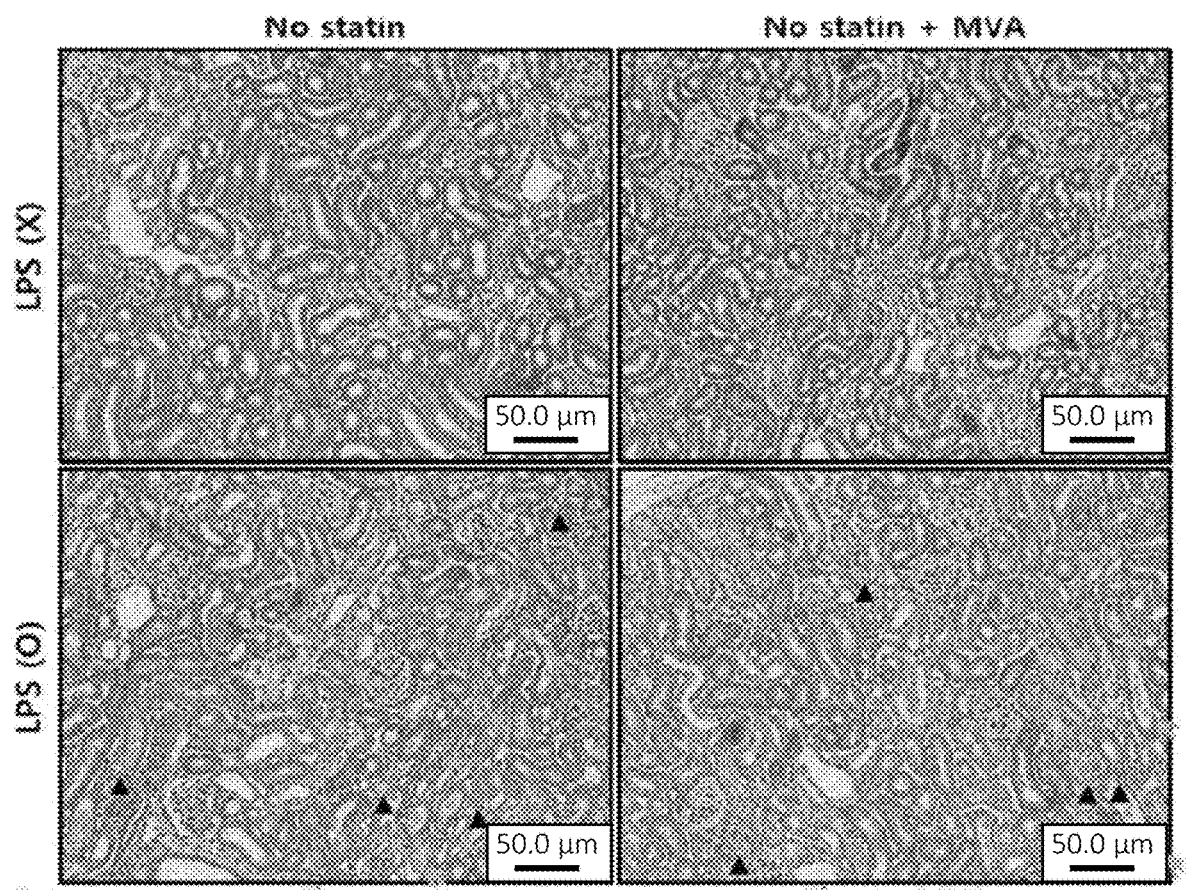
FIGS. 17 and 18 show the results of H & E staining performed to evaluate the effects of an isoprenoid-based compound on the prevention and treatment of statin-induced adverse effects in vivo according to an Example of the present disclosure.
Figure 18:
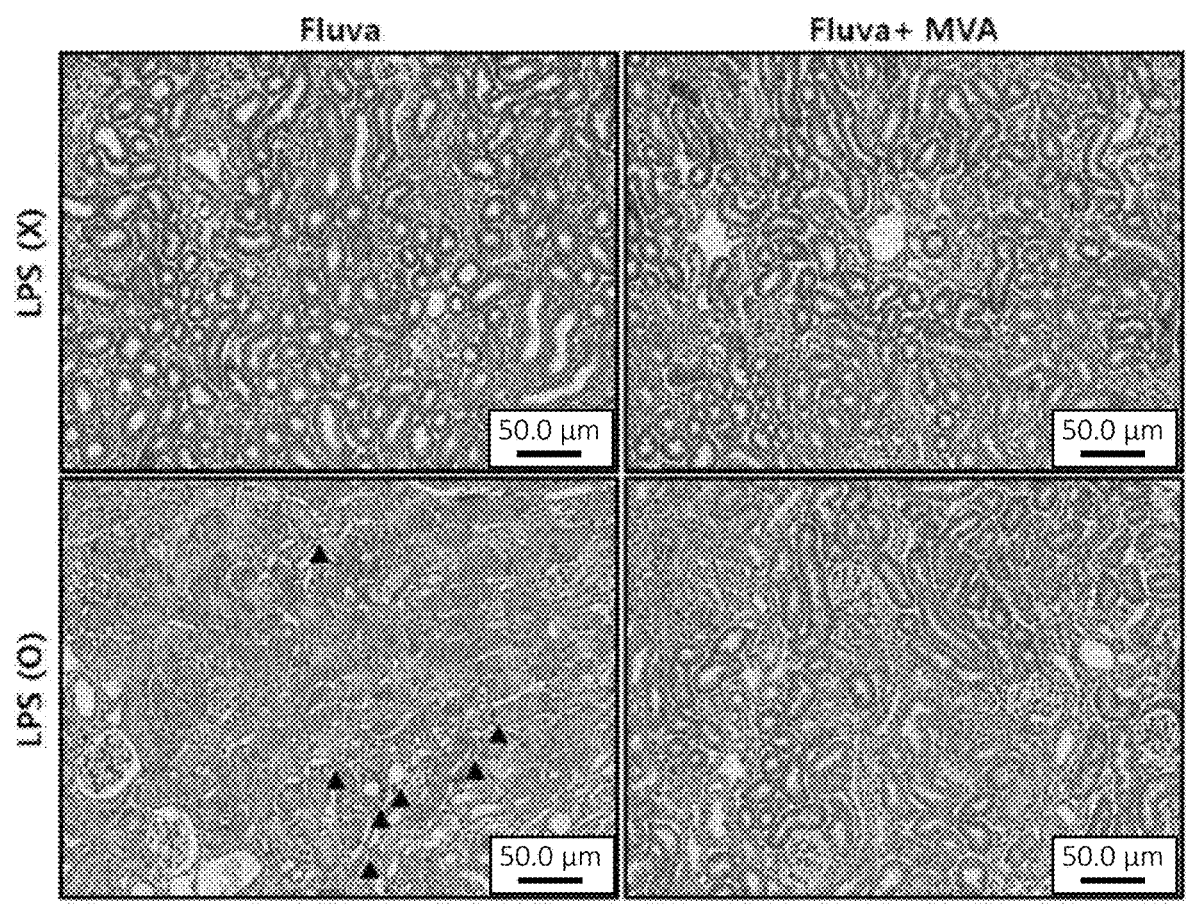
Figure 19:
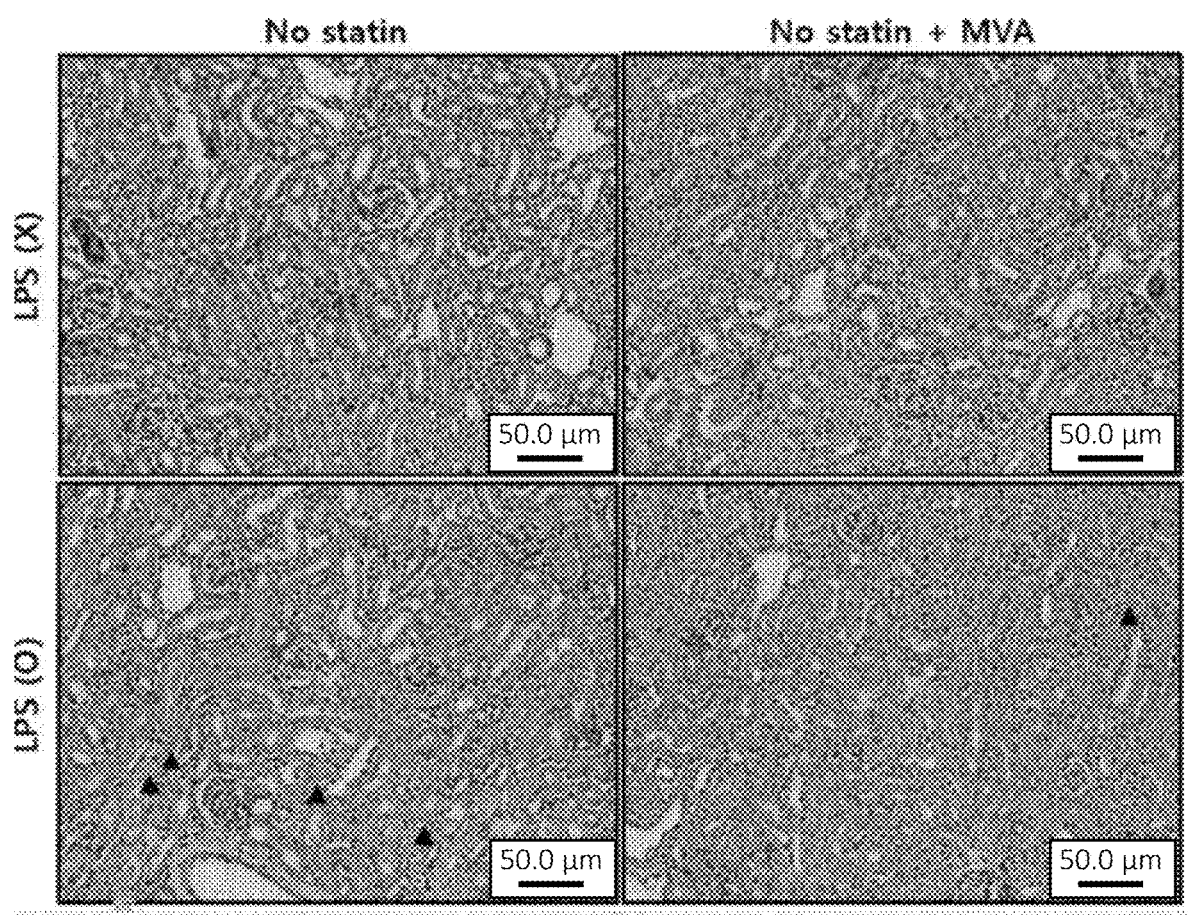
FIGS. 19 and 20 show the results of PAS staining performed to evaluate the effects of an isoprenoid-based compound on the prevention and treatment of statin-induced adverse effects in vivo according to an Example of the present disclosure.
Figure 20:
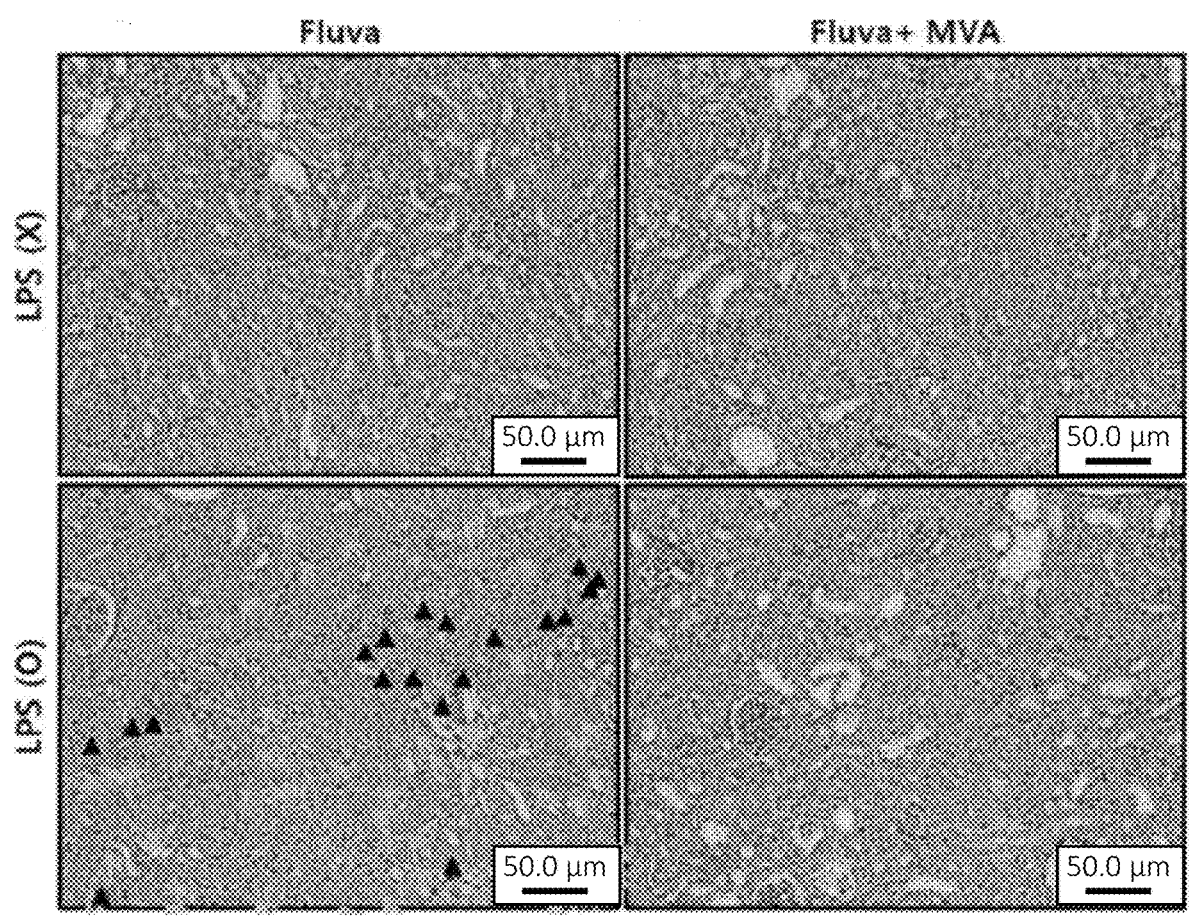
Figure 21:
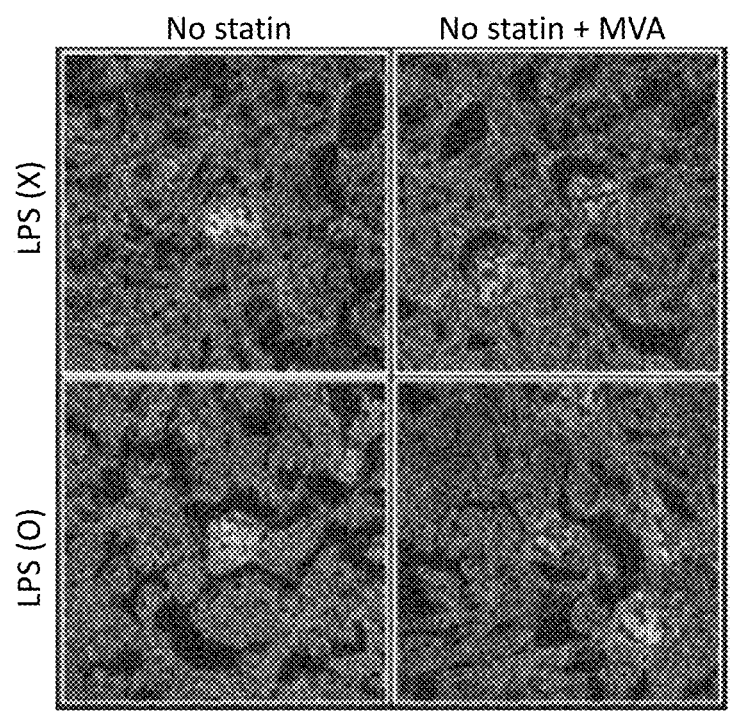
FIGS. 21 and 22 show the results of NGAL immunohistochemistry performed to evaluate the effects of an isoprenoid-based compound on the prevention and treatment of statin-induced adverse effects in vivo according to an Example of the present disclosure.
Figure 22:
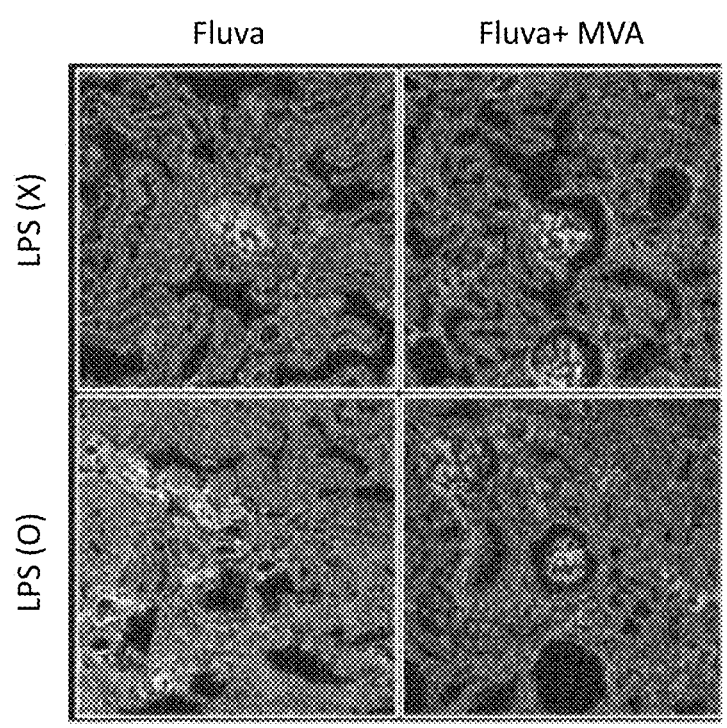

FIG. 17 shows the results of performing H & E staining, and FIGS. 19 and 20 show the results of performing PAS staining. In the figures, the azure arrow indicates the site where a cast was formed, and the blue arrowhead indicates the site where tubule cell vacuolization was induced. FIGS. 21 and 22 show the results of performing NGAL immunohistochemistry. In the figures, red represents phalloidin indicating the tubule structure, green represents NGAL, and blue represents DAPI indicating the cell nucleus. In addition, FIG. 23 is a graph showing the results of quantifying NGAL staining.

As shown in FIGS. 17 to 20, it was confirmed that in the experimental mouse group in which the oxysterol was formed by administering only the lipopolysaccharide without administering the statin, cast formation and tubule cell vacuolization were induced, and in the experimental mouse group in which the oxysterol was formed after administering the statin, cast formation and tubule cell vacuolization were further induced. In addition, from the results of administering mevalonate (MVA), it was confirmed that the mevalonate (MVA) showed no therapeutic effect on kidney damage caused by oxysterol formation, but exhibited a significant effect in the experimental group to which the statin and the oxysterol were co-administered.

Figure 23:
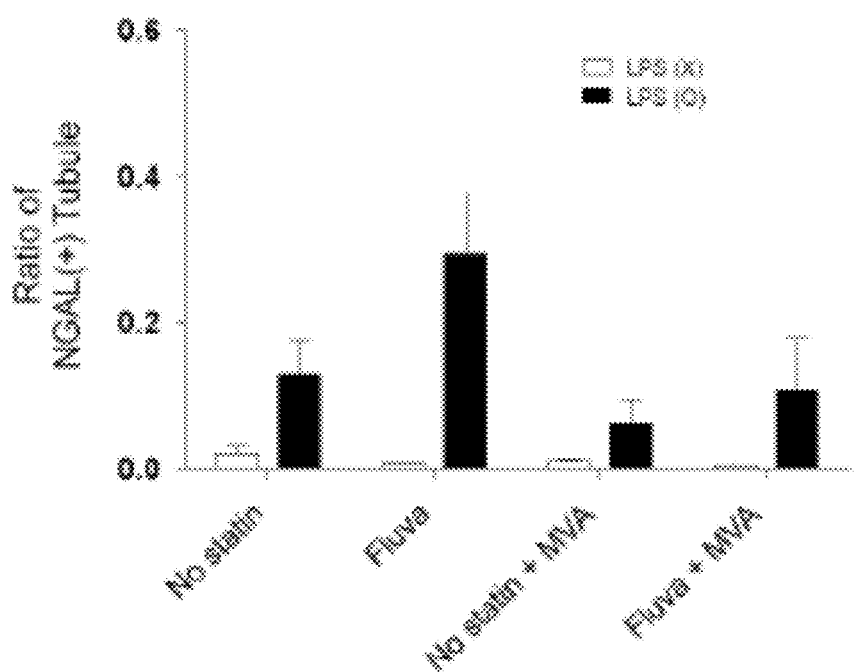
FIG. 23 is a graph showing the results of quantifying the results of NGAL immunohistochemistry according to an Example of the present disclosure.

As shown in FIGS. 21 to 23, it was confirmed that when generation of the oxysterol was induced without administration of the statin, the expression of NGAL, an early diagnostic marker of acute renal failure, increased, but when generation of the oxysterol was induced after administration of the statin, the expression of NGAL significantly increased. In addition, it was confirmed that when mevalonate (MVA) was administered to the experimental group in which generation of the oxysterol was induced without administration of the statin, the mevalonate (MVA) showed no significant therapeutic effect, but when the mevalonate (MVA) was administered to the experimental group in which generation of the oxysterol was induced after administration of the statin, the expression of NGAL significantly decreased.

In addition, it was confirmed that in the mice to which the statin was administered alone, the concentrations of total cholesterol and low-density lipoprotein decreased compared to those in the control group to which the statin was not administered, and in the group to which the statin and the oxysterol were co-administered, the concentrations of total cholesterol and low-density lipoprotein decreased, but damage to kidney tissue was observed. Furthermore, it was confirmed that in the experimental group to which the statin, the oxysterol and the mevalonate (MVA) were all administered, the concentrations of total cholesterol and low-density lipoprotein decreased, but kidney tissue was not damaged. From the above results, it could be confirmed that the isoprenoid-based compound effectively reduced the adverse effects of the statin while maintaining the therapeutic effect of the statin.

Through the above results, it could be confirmed that the adverse effects (cell damage in the kidney, pancreas, nerve, etc.) of a low concentration of the statin, that is, the statin at a defined daily dose usable for treatment, significantly increased in the presence of the oxysterol in vivo, and the isoprenoid-based compound or zaragozic acid could effectively prevent and treat the adverse effects of the statin. In addition, it could be confirmed that in cell damage caused by the oxysterol alone, the isoprenoid-based compound showed no preventive or therapeutic effect, but in adverse statin effects in the presence of the oxysterol, the isoprenoid-based compound significantly reduced cell damage. Therefore, it could be confirmed that the isoprenoid-based compound or zaragozic acid of the present disclosure may be effectively used to prevent adverse effects that may be caused by administration of a low concentration of statin, or to treat the adverse effects that occurred.

Although the present disclosure has been described in detail with reference to the specific features, it will be apparent to those skilled in the art that this description is only of a preferred embodiment thereof, and the scope of the present disclosure is limited thereto. Thus, the substantial scope of the present disclosure will be defined by the appended claims and equivalents thereof.

INDUSTRIAL APPLICABILITY

The pharmaceutical composition, the pharmaceutical composition for co-administration with statin and the method of treating by administering the same according to the present disclosure may prevent and/or treat adverse statin effects that can be induced by statin, that is, can be induced at any time by oxisterols present at abnormal levels in the body. They can not only treat but also prevent the adverse effects of statin therapeutics whose use has recently increased rapidly, and thus it is expected that they can be widely used for various diseases and the utilization thereof can further be increased.

The invention claimed is:

1. A method for preventing or treating statin-induced adverse drug reactions, the method comprising administering to a subject in need thereof a pharmaceutically effective amount of an isoprenoid-based compound, wherein the isoprenoid-based compound is any one or more selected from the group consisting of farnesyl pyrophosphate, mevalonate, isopentenyl pyrophosphate, and geranylgeranyl pyrophosphate.

2. The method of claim 1, wherein the statin is any one selected from the group consisting of atorvastatin, rosuvastatin, simvastatin, pitavastatin, pravastatin, fluvastatin, lovastatin, cerivastatin, and mevastatin.

3. The method of claim 1, wherein the adverse drug reactions are caused by statin administration in a state in which oxysterols produced in vivo by lipopolysaccharides are abnormally increased compared to those in normal people.

4. The method of claim 3, wherein the adverse drug reactions are caused by damage to any one or more cells selected from the group consisting of kidney tubule cells, nerve cells, and pancreatic cells.

5. The method of claim 4, wherein a disease caused by the damage to kidney tubule cells is any one selected from the group consisting of acute renal failure, acute tubular necrosis injury, and ischemic reperfusion injury.

6. The method of claim 4, wherein a disease caused by the damage to nerve cells is any one selected from the group consisting of cognitive dysfunction, dementia, Parkinson's disease, Alzheimer's disease, Huntington's syndrome, stroke, and spinal nerve damage.

7. The method of claim 4, wherein a disease caused by the damage to pancreatic cells is diabetes.

8. The method of claim 3, wherein oxysterols produced in vivo by lipopolysaccharides are abnormally increased due to the inflammation.

9. The method of claim 1, further comprising administering a pharmaceutically effective amount of statin to the subject in need thereof.

10. The method of claim 9, further comprising administering an ezetimibe formulation, a niacin extended-release formulation, or an amlodipine formulation to the subject in need thereof.

11. The method of claim 1, wherein the adverse drug reactions are damage to kidney tubule cells, nerve cells or pancreatic cells caused by statin administration in a state in which oxysterols produced in vivo by lipopolysaccharides are abnormally increased compared to those in normal people.

12. The method of claim 11, wherein the oxysterols produced in vivo by lipopolysaccharides are abnormally increased due to inflammation.

* * * * *